United States Patent [19]
Abidin et al.

[11] Patent Number: 5,507,762
[45] Date of Patent: *Apr. 16, 1996

[54] METHOD OF DISPENSING AND DISPOSING OF BLADES DURING A SURGICAL PROCEDURE AND GUARDING AGAINST INADVERTENT CUTS DURING USE THEREOF

[75] Inventors: Michael R. Abidin; Steven P. Lehmbeck, both of Baltimore, Md.

[73] Assignee: Leonard Bloom, Towson, Md.; a part interest

[ * ] Notice: the term of the patent shall not extend beyond the expiration date of Pat. No. 5,361,902.

[21] Appl. No.: 307,404

[22] Filed: Sep. 16, 1994

Related U.S. Application Data

[60] Continuation of Ser. No. 113,434, Aug. 27, 1993, abandoned, which is a division of Ser. No. 894,595, Jun. 5, 1992, Pat. No. 5,361,902.

[51] Int. Cl.⁶ .................................................. A61B 17/32
[52] U.S. Cl. ........................... 606/167; 206/370; 206/363; 206/354; 206/359
[58] Field of Search ........................... 606/167; 128/898; 206/363, 370, 356, 354, 355, 359

[56] References Cited

U.S. PATENT DOCUMENTS

| | | | |
|---|---|---|---|
| 3,447,181 | 6/1969 | Coker et al. | 206/363 X |
| 4,106,620 | 8/1978 | Brimmer et al. | 206/363 |
| 4,576,164 | 3/1986 | Righeson | 606/167 |

Primary Examiner—Michael H. Thaler
Attorney, Agent, or Firm—Leonard Bloom

[57] ABSTRACT

A sterile blade dispenser facilitates removal of dulled used blades, as well as the mounting of sharp unused blades, on a scalpel during a surgical procedure being conducted in an operating room or similar environment. Preferably, the scalpel has a sliding retractable guard, and the combination of the guarded scalpel and the blade dispenser precludes inadvertent cuts or nicks during the surgical procedure.

4 Claims, 12 Drawing Sheets

METHOD OF DISPENSING AND DISPOSING OF BLADES DURING A SURGICAL PROCEDURE AND GUARDING AGAINST INADVERTENT CUTS DURING USE THEREOF

This application is a continuation, of application Ser. No. 08/113,434, filed Aug. 27, 1993, now abandoned, which is a division of application Ser. No. 07/894,595, filed Jun. 5, 1992, now U.S. Pat. No. 5,361,902.

FIELD OF THE INVENTION

The present invention relates to a surgical blade dispenser and disposal system for use during an operating procedure, and more particularly, to a surgical blade dispenser and disposal system for use in conjunction with a guarded scalpel.

BACKGROUND OF THE INVENTION

Surgical blades on a scalpel are replaced several times during an operating procedure. On the average, about five new blades are used on each scalpel, depending upon the surgeon's techniques and preferences, the type of operation being performed, and the severity thereof. During the procedure, the blade can become dulled quite rapidly, especially if tissue or bone is being cut, and surgeons prefer to have a very sharp blade on the scalpel at all times.

Each blade is contained in a sterile package of aluminum foil or the like, and the package is peeled apart to uncover the rear portion of the blade. Typically, the rear portion of the blade has a longitudinal slotted opening formed therein to receive a laterally-projecting bar on the forward portion of the scalpel; and the bar on the scalpel is snapped into the slotted recess on the blade, thereby removably mounting the blade on the scalpel.

This is a manual operation. The used blade is removed from the scalpel, and a new blade is subsequently mounted on the scalpel, basically using finger dexterity, and sometimes using an instrument called a hemostat. Despite the care that is exercised, the nurse or other assistant in the operating room is occasionally cut or nicked while changing blades on a scalpel, especially while the nurse or assistant is concentrating on the patient or the instruments at critical times during the operating procedure.

The used blades often carry blood, tissue or bodily fluids, and thus there is a substantial problem that the nurse or other assistant in the operating room will inadvertently acquire an infectious disease, such as the Hepatitis B virus or the HIV ("AIDS") virus. The situation is becoming quite serious, if not alarming, and some health care providers have quit their operating room practice entirely rather than continually risking exposure to the AIDS virus.

SUMMARY OF THE INVENTION

Accordingly, it is an object of the present invention to provide a blade dispenser and disposal system that speeds up the process of changing blades during a surgical procedure in an operating room or the like, thereby assuring that the surgeon will at all times have a "fresh" sharp blade.

It is another object of the present invention to provide a surgical blade dispenser that is convenient and easy to use, reliable, and economical to manufacture.

In accordance with the teachings of the present invention, there is herein illustrated and described, a preferred embodiment of a blade dispenser and disposal system for use during a surgical procedure in an operating room or the like, wherein the blades on a scalpel are normally replaced during the procedure to maintain good surgical cutting techniques. The dispenser includes a housing, and a first means is provided within the housing to enable an existing blade to be removed from the scalpel upon insertion and withdrawal of the scalpel from the housing, the existing discarded blade being confined within the housing. At least one new blade is provided in the housing, and a second means is provided within the housing to enable the new blade to be mounted on the scalpel upon subsequent re-insertion of the scalpel into the housing and withdrawal of the scalpel therefrom. As a result, inadvertent cuts or the like are precluded as the blades are replaced on the scalpel during the surgical procedure.

In accordance with a preferred embodiment of the present invention, a sterile package is provided for the housing, the sterile package being removed prior to the surgical procedure.

Preferably, a plurality of new blades is contained within the housing; and the housing with the discarded blades confined therein, as well as any unused blades, is disposed of following the surgical procedure.

In accordance with the further teachings of the present invention, and fully compatible therewith, a guard is slidably mounted on the scalpel, the guard being alternatively retracted and advanced to uncover and cover the blade, respectively, all in a one-handed operation. As a result, inadvertent cuts or the like are precluded in passing the scalpel from the assistant to the surgeon, and vice-versa, during the surgical procedure.

Accordingly, the blade is exposed only when the scalpel is being used by the surgeon during the surgical procedure.

Viewed in another aspect, the present invention provides, in a surgical procedure in an operating room or the like, a method of changing blades on a scalpel during the surgical procedure and transferring the scalpel from an assistant to a surgeon during the procedure to avoid inadvertent cuts or the like. The inventive method including the steps of providing a sterile blade package and further providing a guarded scalpel. The sterile blade package is opened in the operating room, and the guard is moved on the scalpel to an unguarded "off" position. The unguarded scalpel is inserted into the package to strip an "old" or used blade from the scalpel. The stripped scalpel is removed from the package and re-inserted into the package to pick up a "new" or unused blade. The scalpel with the new blade is removed from the package, and the guard on the scalpel is moved to a guarded "on" position.

Viewed in yet another aspect, the present invention provides (for use with a surgical scalpel having a replaceable blade) the combination of a manually-operable guard means on the scalpel—such that the blade on the scalpel may be covered when the scalpel is transferred from the assistant to the surgeon (and vice versa) during a surgical procedure in an operating room in a hospital or similar environment—and a dual-purpose blade dispenser and collector for the disposal of old or used blades. The scalpel may be inserted into the dispenser to strip a used blade from the scalpel and to subsequently pick up a new unused blade, such that the blade is exposed only when the scalpel is being used by the surgeon during the procedure.

These and other objects of the present invention will become apparent from a reading of the following specification taken in conjunction with the enclosed drawings.

BRIEF DESCRIPTION OF THE DRAWINGS

FIG. 1 is a perspective of the lead surgeon, assistants and nurses performing a surgical procedure in an operating room in a hospital, clinic or the like.

GENERAL DESCRIPTION OF THE PREFERRED EMBODIMENTS

Figure 1:
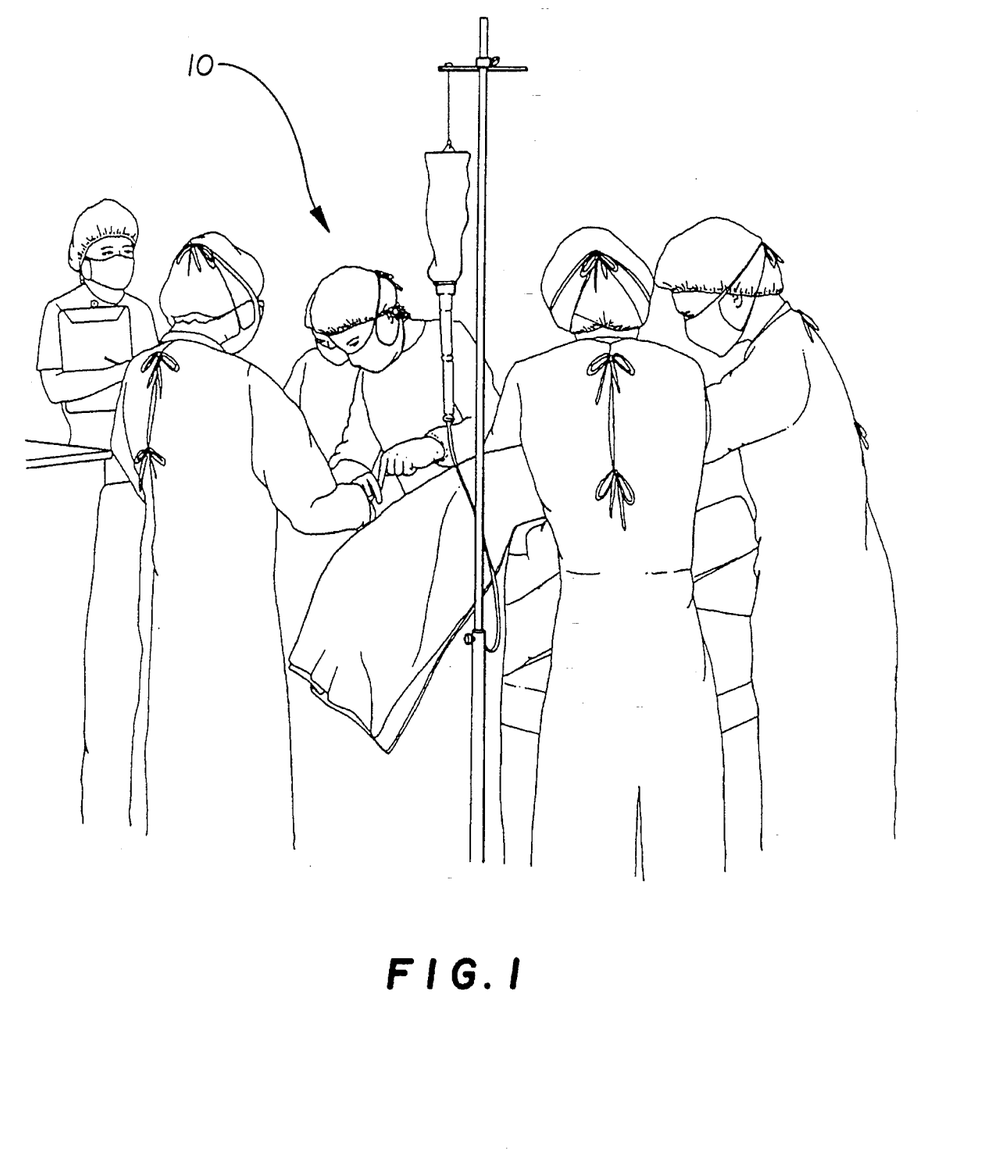
Figure 2:
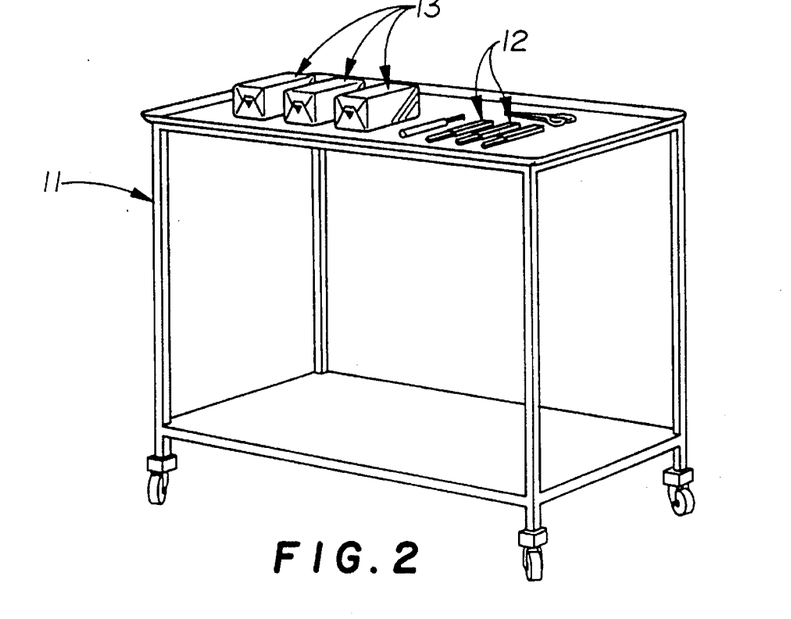
FIG. 2 is a perspective view of a typical wheeled cart used in the operating room to hold the various surgical devices and instruments, including one or more scalpels and one or more sterile blade packages of the present invention.
Figure 3:
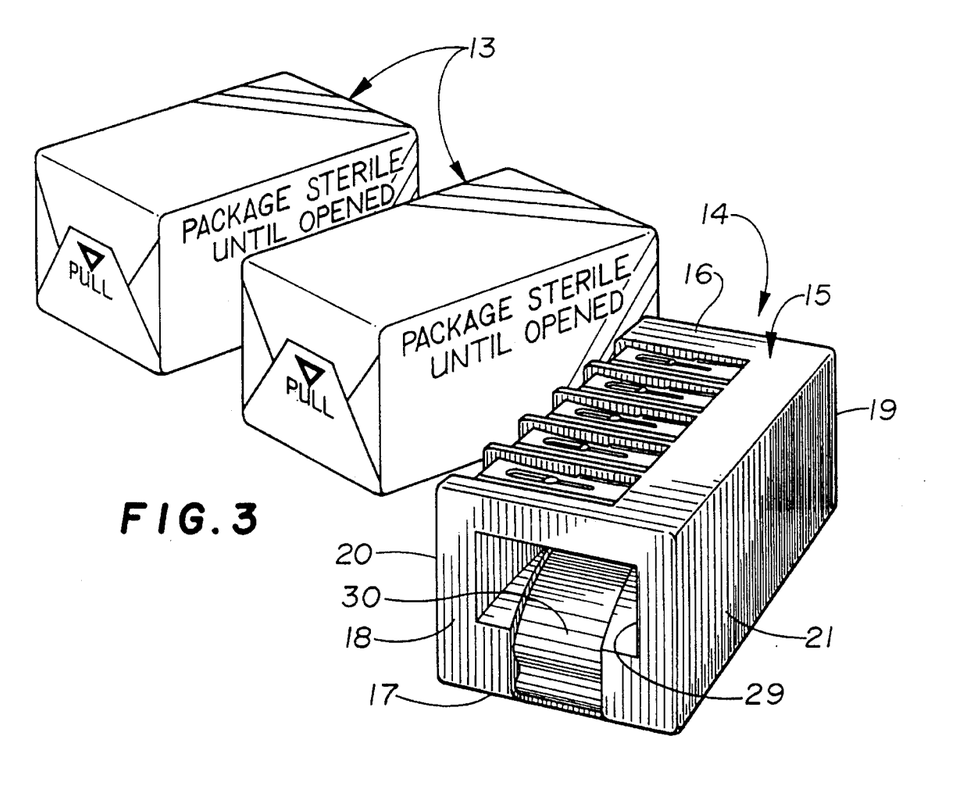
FIG. 3 is a perspective view of the sterile blade packages of FIG. 2, drawn to an enlarged scale, and further showing the sterile packaging removed from one of the packages to uncover the blade dispenser and collector of the present invention.
Figure 4:
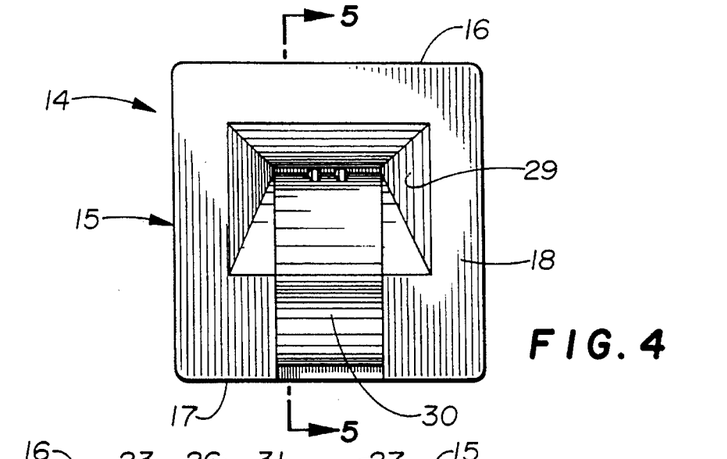
FIG. 4 is a front view of housing of the blade dispenser of FIG. 3, drawn to a somewhat enlarged scale.

With reference to FIGS. 1–3, the present invention is intended for use in an operating room 10 in a hospital, clinic or similar area. Within the operating room 10, there is usually a wheeled cart or tray 11 upon which the various surgical instruments or devices are placed. These devices include a number of scalpels 12 as well as the sterile blade packages 13 of the present invention. The packaging is removed from one of the sterile blade packages, as shows more clearly in FIG. 3, to uncover a blade cartridge or dispenser 14 of the present invention.

With reference again to FIG. 3, and with further reference to FIGS. 4–8, the blade dispenser 14 is preferably molded and fabricated from a suitable plastic material and is preferably oblong or rectangular in shape. However, it will be appreciated that the blade dispenser 14 may have any convenient size and shape and may be fabricated from a variety of suitable materials, if desired. With this in mind, the blade dispenser 14 includes a housing 15 having a top wall 16, a bottom wall 17, a front wall 18, a rear wall 19, a right side wall 20 and a left side wall 21.

Figure 5:
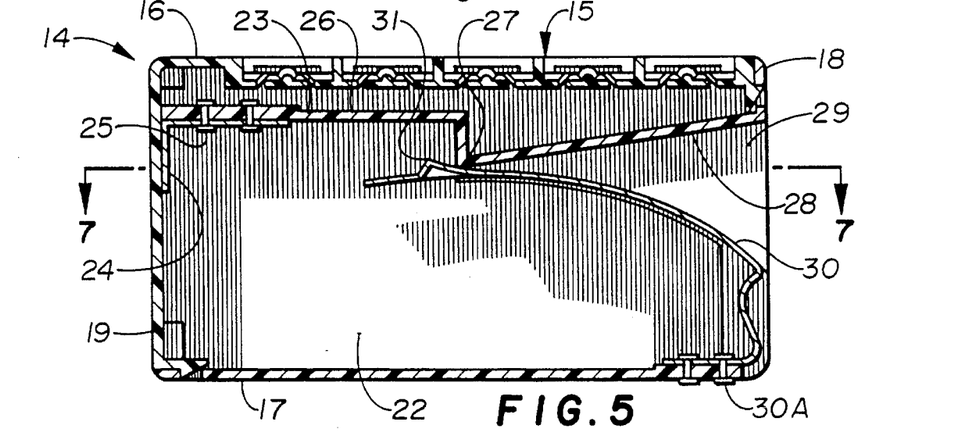
FIG. 5 is a cross-sectional view, taken along the lines 5—5 of FIG. 4, and showing an internal wall intended to cooperate with a leaf spring in the housing to remove an "old" or used blade from the scalpel.

As best shown in FIG. 5, the housing 15 has a chamber 22 for receiving the "old" or used blades. The housing 15 further has an internal wall 23 disposed below the top wall 16 and running from the rear wall 19 of the housing 15 to the front wall 18 thereof. Preferably, this internal wall 23 is molded from a suitable plastic material and is cantilever mounted on the rear wall 19 by means of an L-shaped bracket 24 suitably secured to the rear wall 19 and, in turn, to the internal wall 23 by rivets 25. The internal wall 23 includes a straight portion 26, a downwardly-projecting intermediate portion providing a shoulder 27, and an upwardly-sloping portion 28 terminating at the front wall 18 of the housing 15. The housing 15 has an opening 29 in its front wall 18 through which the scalpel may be inserted (as hereinafter described) to remove or strip the "old" or used blade from the scalpel.

Figure 7:
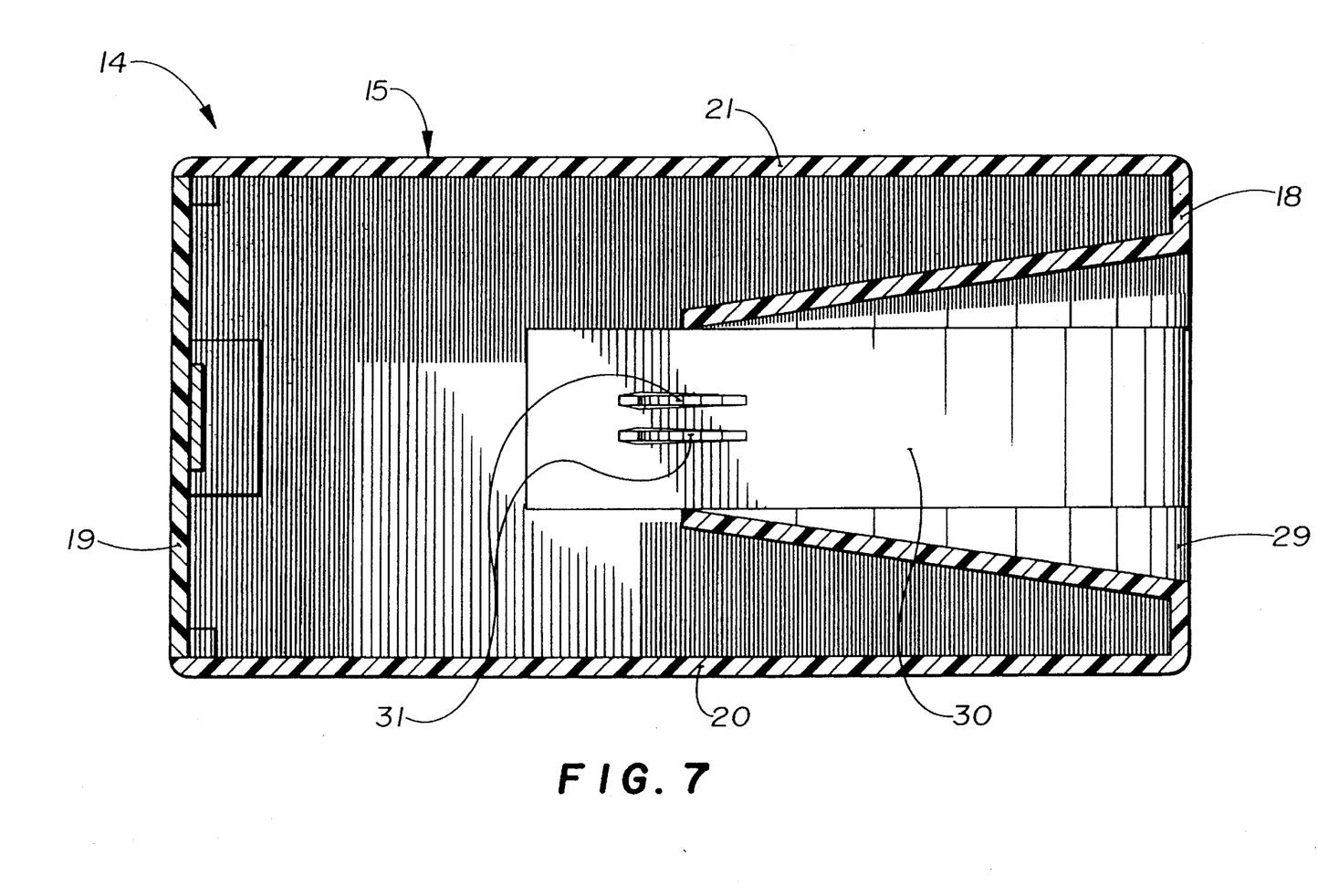
FIG. 7 is a cross-sectional view, taken along the lines 7—7 of FIG. 5 and drawn to an enlarged scale, and showing a pair of lanced out upwardly-projecting fingers on the leaf spring.
Figure 8:
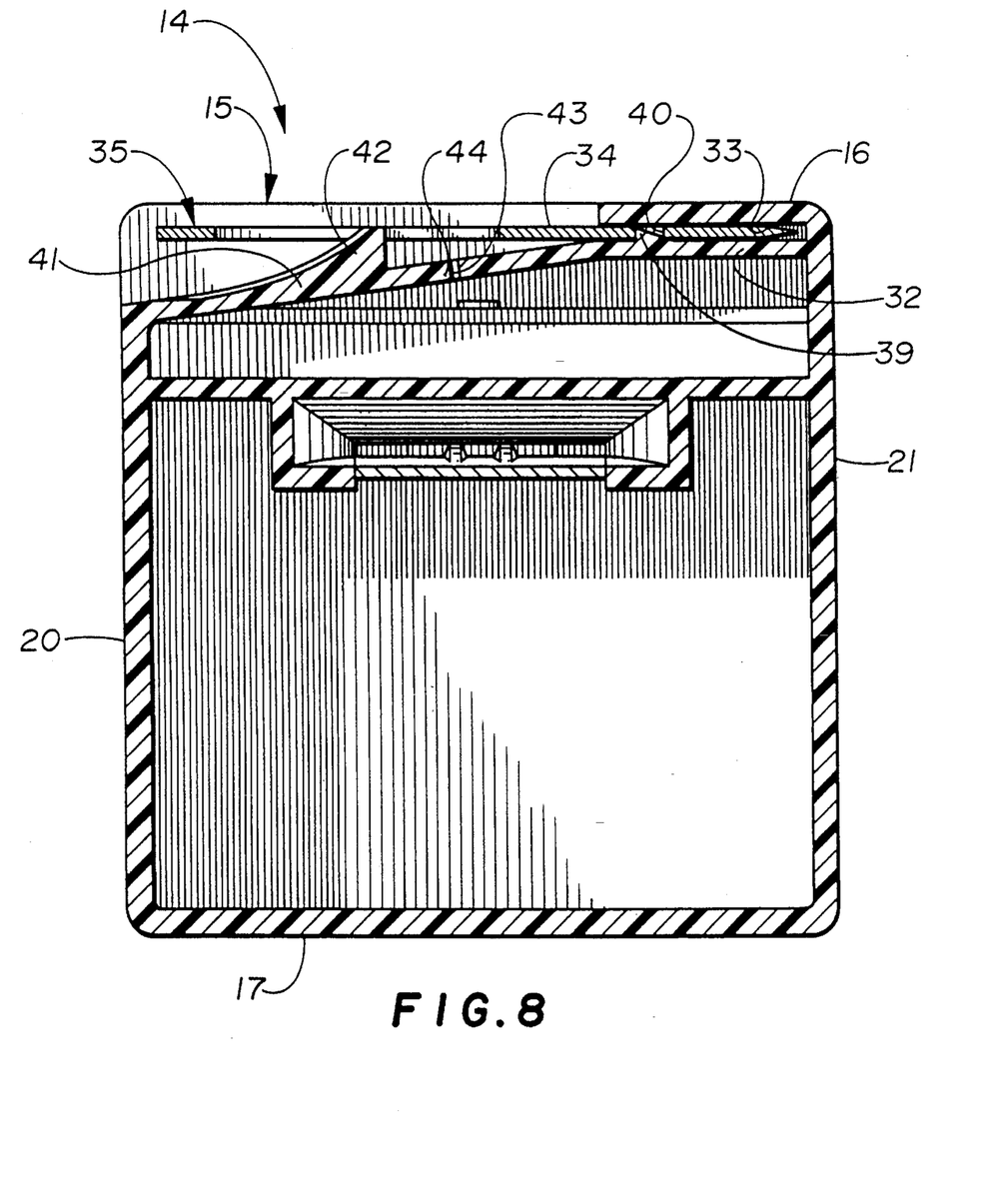
FIG. 8 is a cross-sectional view, taken along the lines 8—8 of FIG. 6, and showing the retention of a new blade in the housing.

With reference again to FIG. 5, and with further reference to FIG. 7, a leaf spring 30 is cantilever mounted on the bottom wall 17 of the housing by rivets 30A (or other suitable means) and the leaf spring 30 is disposed below the internal wall 23 in the housing 15, above the chamber 22 therein, and extends from the opening 29 in the front wall 18 of the housing 15 towards the rear wall 19 thereof. The leaf spring 30 has a pair of upwardly-projecting lanced-out fingers 31 formed thereon, as shown more clearly in FIGS. 5 and 7.

With reference again to FIGS. 6 and 8, the housing 15 of the blade dispenser 14 has a first interior wall 32 formed therein, recessed below the top wall 16 of the housing 15, and extending from the left side wall 21 of the housing 15 towards the right side wall 20 thereof. As a result, and as shown more clearly in FIG. 8, the top wall 16 of the housing 15 and the first interior wall 32 thereof define therebetween a slotted recess 33 in the housing 15 for receiving the forward portion 34 of a blade 35.

With reference to FIGS. 9–12, the blade 35 includes a rearward portion having a longitudinal slotted opening 36 formed therein. This opening 36 is conventional and includes a rearward portion 36A and a forward (narrower) portion 36B. The scalpel, on the other hand, has a forward portion cleat provided with externally-accessible opposing slots or grooves 37A and 37B, respectively. In the usual practice of mounting the blade 35 on the forward portion of the scalpel 12, the blade 35 is flexed slightly so that the narrower forward portion 36B of the slotted opening 36 in the blade 35 is received in the grooves 37A and 37B of the scalpel 12.

Figures 9, 10, 11:
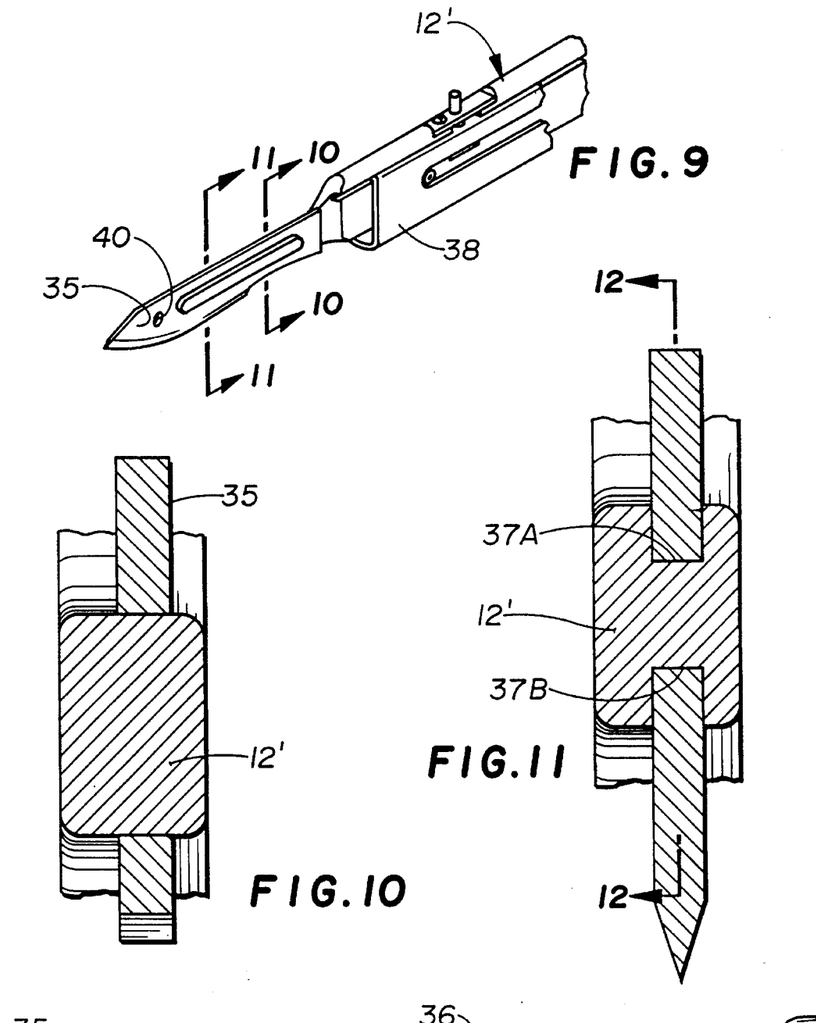
FIG. 9 is a perspective view of a guarded scalpel with which the teachings of the present invention may find more particular utility, the guard being slidably retracted rearwardly of the scalpel to uncover the blade which is mounted on a forwardly-projecting portion of the scalpel.
FIG. 10 is a cross-sectional view, taken across the lines 10—10 of FIG. 9 and drawn to an enlarged scale, and showing the removable mounting of the blade on the forward portion of the scalpel.
FIG. 11 is a further cross-sectional view, taken across the lines 11—11 of FIG. 9 and drawn to an enlarged scale, and further showing the removable mounting of the blade on the scalpel.
Figure 12:
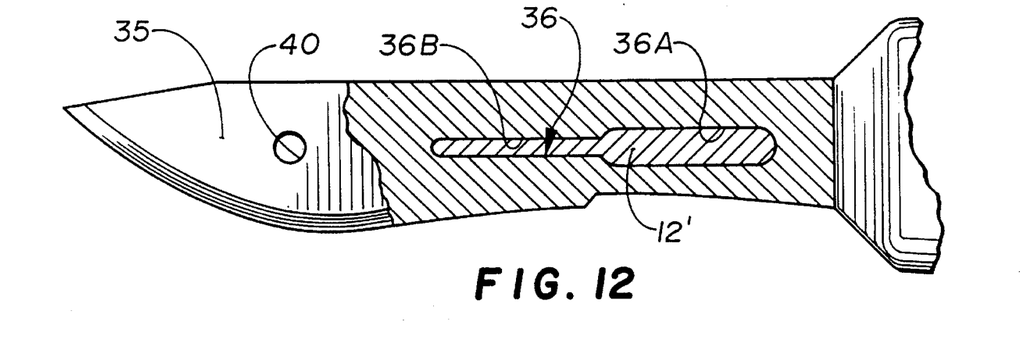
FIG. 12 is a still further cross-sectional view, taken across the lines 12—12 of FIG. 11.

Preferably, but not necessarily, the blade dispenser 14 of the present invention may find more particular utility in conjunction with a guarded scalpel $12^1$ (shown in FIG. 9). This guarded scalpel $12^1$, which is described and claimed in applicant's co-pending application, Ser. No. 825,556 filed Jan. 24, 1992 for now U.S. Pat. No. 5,250,063, "SURGICAL SCALPEL WITH RETRACTABLE GUARD", has a sliding retractable guard 38 for alternatively covering and uncovering the blade 35. The sliding movement of the guard 38 is performed manually, using only one hand, and without requiring the surgeon (or other health care provider) to take his or her eyes off the patient.

With reference again to FIG. 8, the first interior wall 32 has a first upwardly-projecting hook 39 formed thereon; and the hook 39 is received in a circular hole 40 (or other suitable opening) formed in the blade 35, thereby positioning the blade 35 within the slotted recess 33 and preventing the blade 35 from engaging the left side wall 21 of the housing 15. This assures that the blade will remain sharp and will not be dulled, inadvertently, by engaging the walls of the housing 15 and, particularly, the left side wall 21. The housing 15 further has a second interior wall 41 formed therein, recessed below the top wall 16 of the housing 15, and extending from the right side wall 20 of the housing 15 towards the left side wall 21 thereof. The second interior wall 41 has a second upwardly-projecting hook 42 received within the slotted opening 36 in the rearward portion of the blade 35, further positioning and retaining the blade 35 in the housing 15. As shown more clearly in FIG. 8, the first interior wall 32 and the second interior wall 41 have inner extremities 43 and 44, respectively, which confront one another.

Figure 6:
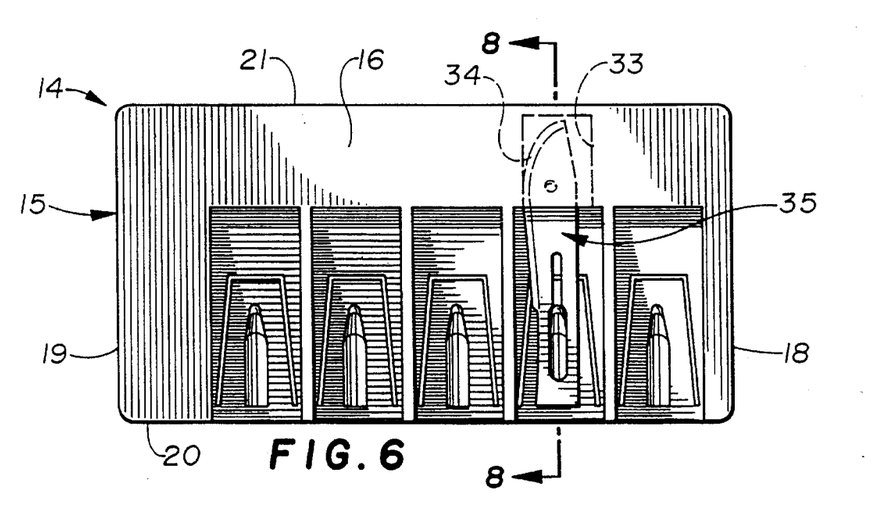
FIG. 6 is a top plan view of the housing of the blade dispenser of the present invention, showing one of the new or unused blades in the dispenser (it being understood that the blade dispenser is intended for a plurality of blades).

Preferably, and as shown more clearly in FIG. 6, the housing 15 of the blade dispenser 14 has five slotted recesses 33 for five blades 35, respectively, as well as five corresponding sets of first and second interior walls 32 and 41, respectively. However, it will be appreciated that any number of replacement blades 35 may be contained within the housing 15 of the blade dispenser 14, consonant with the teachings of the present invention.

Figure 13A:
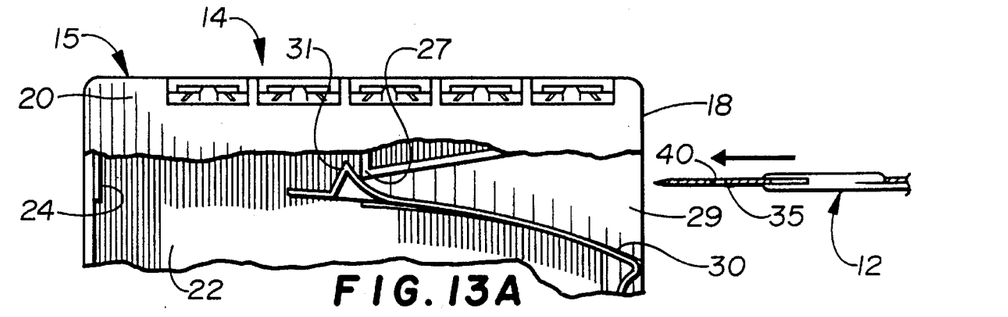
FIG. 13A–13D are schematic sequence views, showing the manner in which the scalpel with an "old" or used blade may be quickly and conveniently inserted into the housing and withdrawn therefrom (in a sliding or reciprocating movement) to remove or "strip" the old used blade from the scalpel.
Figure 13B:
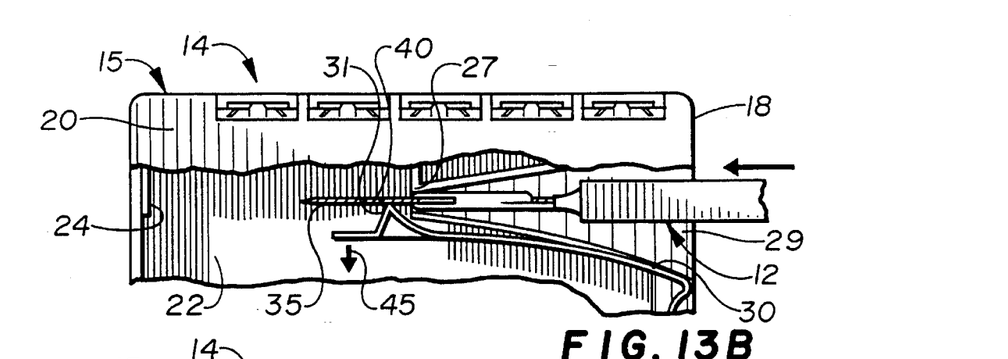
Figure 13C:
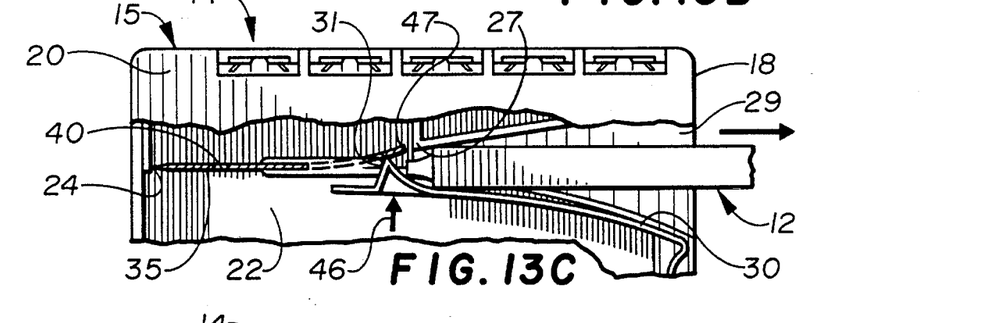
Figure 13D:
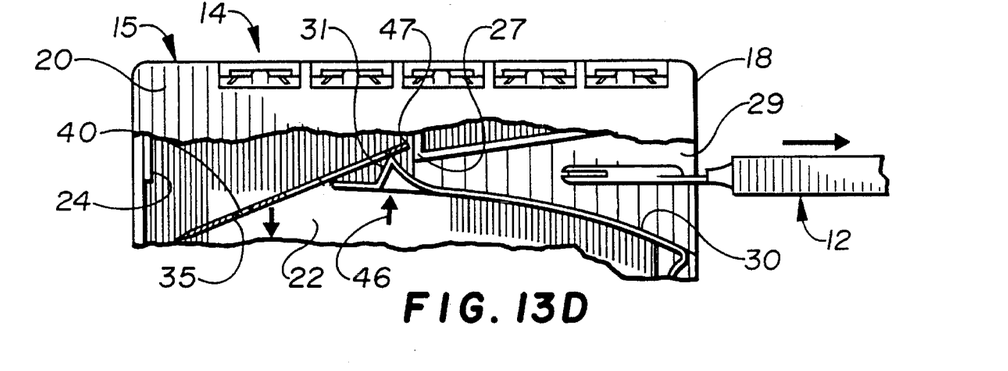

With reference to FIGS. 13A–13D, the sequence of removing or stripping an "old" or used blade 35 from the scalpel 12 will be readily understood. The scalpel 12 (with its used blade 35) is inserted through the opening 29 in the front wall 18 of the housing 15, as shown in FIG. 13A. Preferably, the opening 29 is tapered inwardly (as shown more clearly in FIG. 7) to facilitate insertion of the scalpel 12. As the scalpel 12 is inserted into the housing 15, the used blade 35 on the scalpel 12 deflects the leaf spring 30 downwardly in the housing 15, as shown by the downwardly-projecting arrow 45 in FIG. 13B, and clears the upwardly-projecting fingers 31 on the leaf spring 30 from the shoulder 27 on the interior wall 23 in the housing 15. Thereafter, as the scalpel 12 is withdrawn from the housing 15, as shown more clearly in FIG. 13C, the leaf spring 30 moves upwardly (as indicated by the upwardly-projecting arrow 46 in FIGS. 13C and 13D) such that the end edge 47 of the rearward portion of the blade 35 is bent upwardly (FIG. 13C) and becomes partially disengaged from the scalpel 12; and as the scalpel 12 is further withdrawn from the housing 15, the end edge 47 of the blade 35 encounters the shoulder 27 on the intermediate downwardly-projecting portion of the interior wall 23 in the housing 15, thereby stripping the blade 35 completely from the scalpel 12 as shown more clearly in FIG. 13D. Thereafter, the used blade 35 falls down into the chamber 22 in the housing 15 (and on to the bottom wall 17 thereof) for ultimate disposal with the housing 15 of the blade dispenser 14.

Figure 14A:
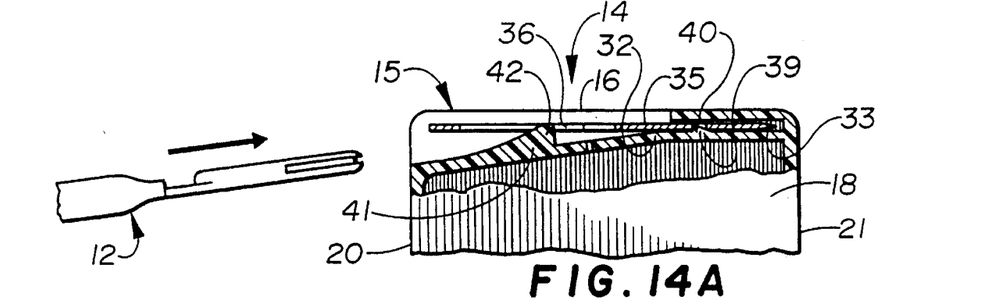
FIGS. 14A–14D are further schematic sequence views, showing the subsequent manner in which the "stripped" scalpel may be reinserted into the housing and withdrawn therefrom, again quickly and conveniently and in a sliding or reciprocating movement, to pick up a "new" or unused blade.
Figure 14B:
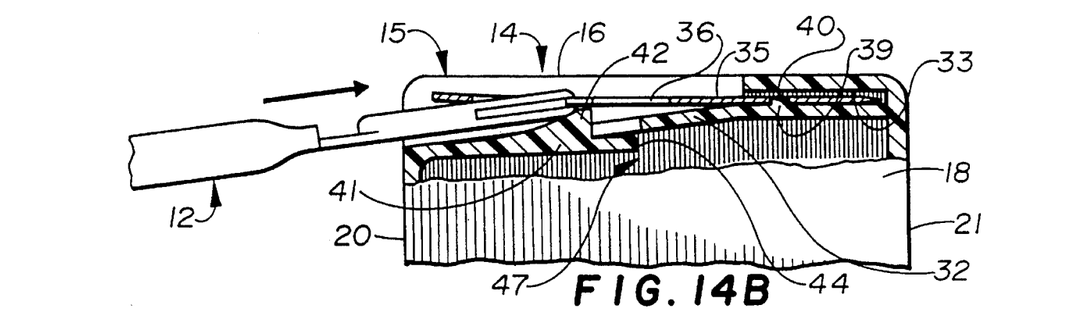
Figure 14C:
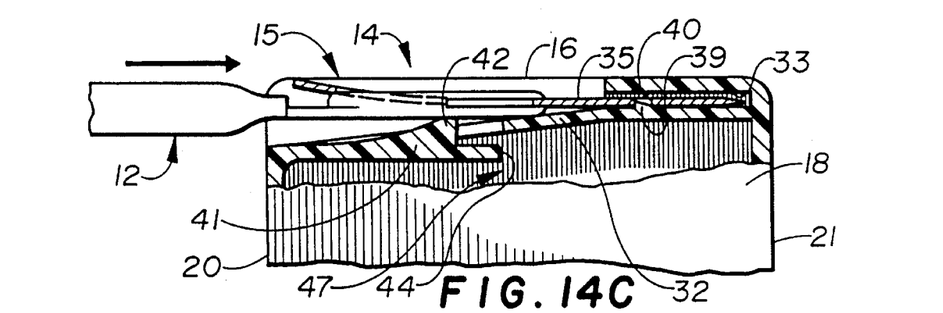
Figure 14D:
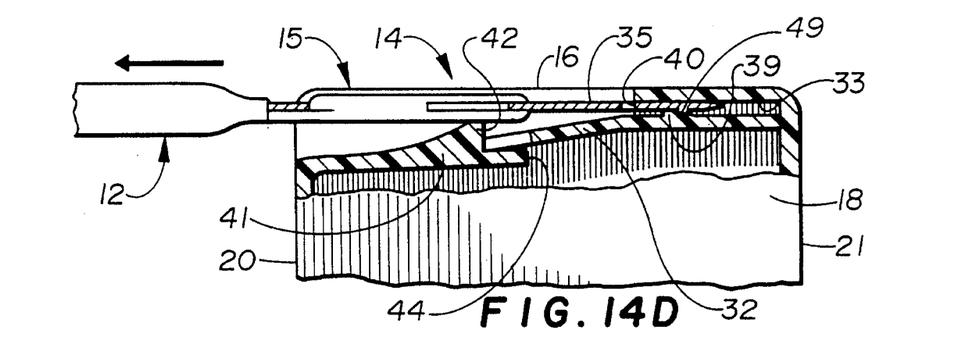

With reference to FIGS. 14A–14D, the sequence of mounting a new ("fresh" or unused) blade 35 on the scalpel 12 will be readily understood. The scalpel 12 (without any blade thereon) is inserted into the right side wall 20 of the housing 15 of the blade dispenser 14, as shown in FIG. 14A. Preferably, the opening in the wall 20 is tapered inwardly (as shown more clearly in FIGS. 6 and 8) to guide the scalpel 12 and facilitate its insertion into the blade dispenser 14. It will be understood by those skilled in the art that the scalpel 12 may be inserted into any suitable wall or opening in the housing 15, and that insertion into the right side wall 20 is only exemplary of the teachings of the present invention. With this in mind, as the scalpel 12 is inserted further into the housing 15, the forward portion of the scalpel 12 deflects the second interior wall 41 downwardly, as indicated by the small downwardly-projecting arrow 47 in FIG. 14B, to disengage the second upwardly-projecting hook 42 from the longitudinal closed slotted opening 36 in the rearward portion of the blade 35. Simultaneously, the forward portion of the scalpel 12 is received in the slotted recess 33 in the housing 15; and as the scalpel 12 is inserted further into the housing 15, as shown in FIG. 14C, the forward portion of the scalpel 12 engages the rearward portion of the blade 35 (rearwardly of its slotted opening 36) and cams the rearward portion of the blade 35 upwardly (again as shown in FIG. 14C). Thereafter, and as shown in FIG. 14D, the forward portion of the scalpel 12 is received in the slotted opening 36 in the blade 35 to mount the blade 35 to the scalpel 12. As scalpel 12 is withdrawn from the housing 15 of the blade dispenser 14, the circular edge of the hole 40 in the forward portion 34 of the blade 35 engages the downwardly-sloping cam surface 49 on the hook 39 and downwardly deflects the first interior wall 32 in the housing 15 (as shown more clearly in FIG. 14D) so that the hook 39 clears the hole 40 in the blade 35. Thereafter, the scalpel 12 (with the "new" blade 35 mounted thereon) may be completely removed from the housing 15 of the blade dispenser 14.

Figure 15A:
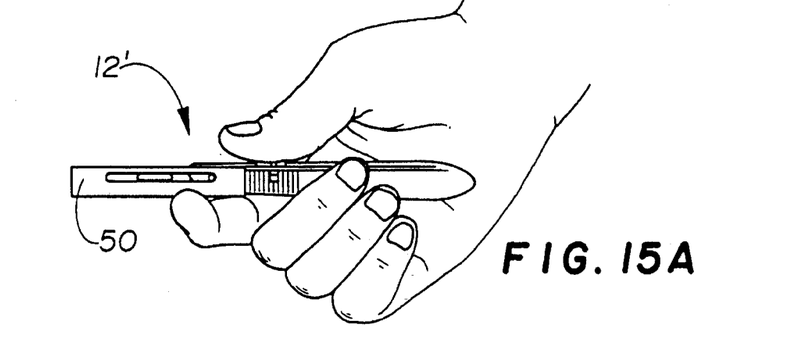
FIGS. 15A–15J are still further schematic sequence views, showing the overall procedure or method involving the preferred guarded scalpel, and basically showing how the guard on the scalpel is moved rearwardly to its unguarded "off" position to uncover the old or used blade, how the scalpel is inserted within the housing and withdrawn therefrom with the used blade removed, how the scalpel is subsequently re-inserted into the housing to pick up an unused blade, and how the guard on the scalpel is moved forwardly to its guarded "on" position, such that the guarded scalpel with its new blade may then be transferred from the nurse to the surgeon during the surgical procedure to avoid inadvertent (and hazardous) cuts and nicks, thereby avoiding the inadvertent acquisition of infectious diseases.
Figure 15B:
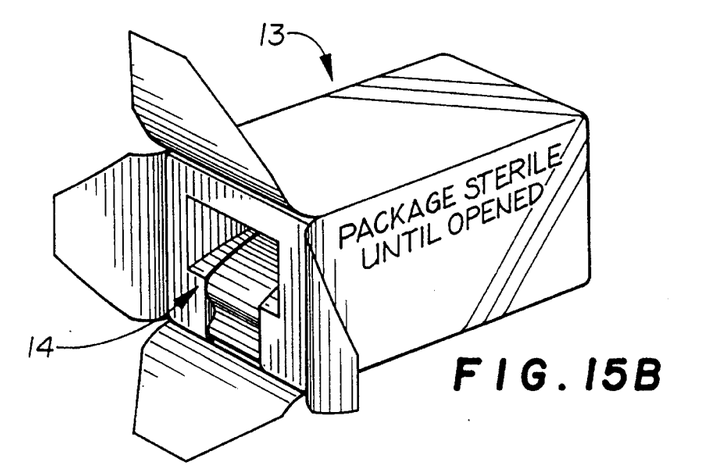
Figure 15C:
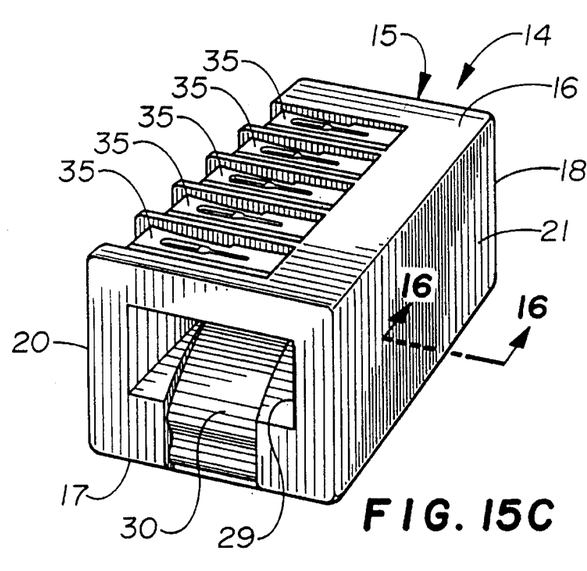
Figure 15D:
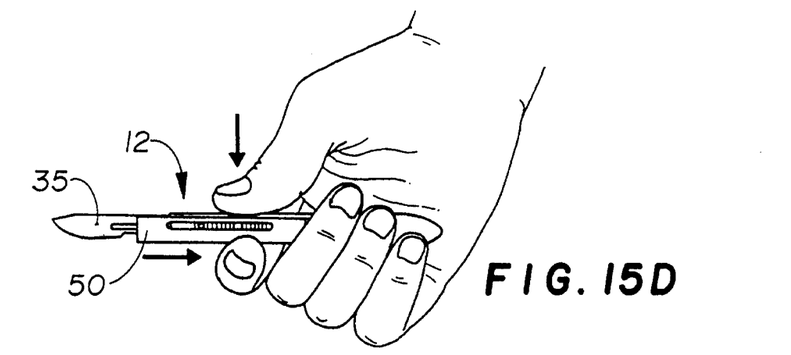
Figure 15E:
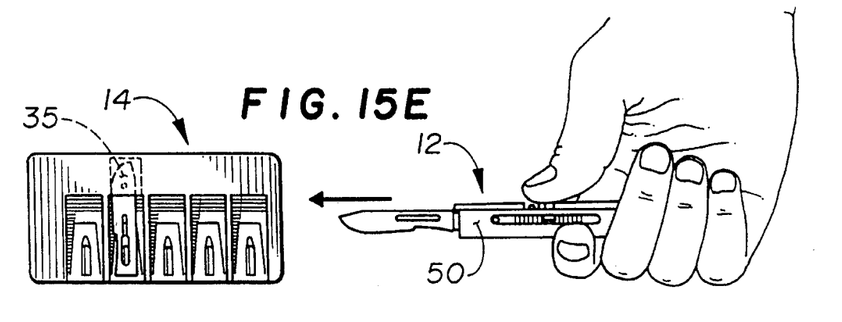
Figure 15F:
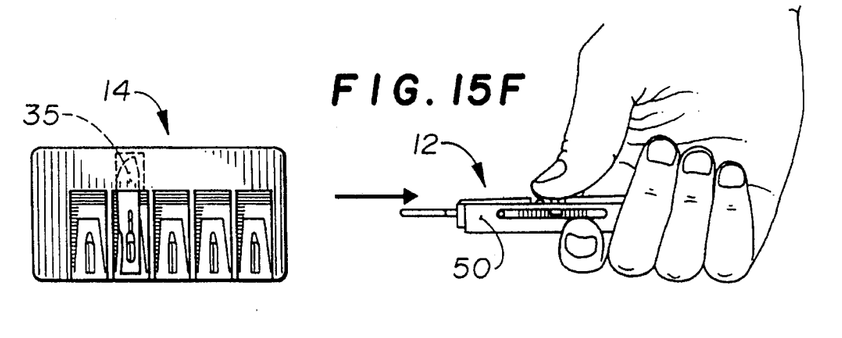
Figure 15G:
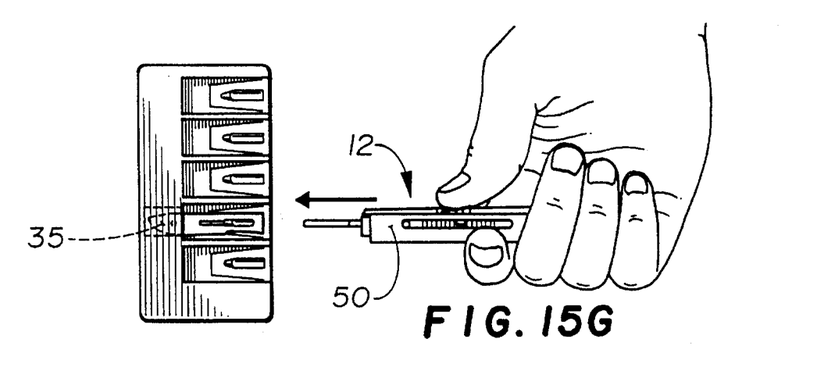
Figure 15H:
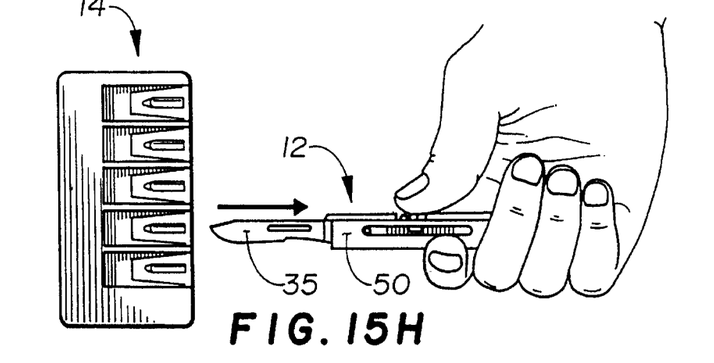
Figure 15I:
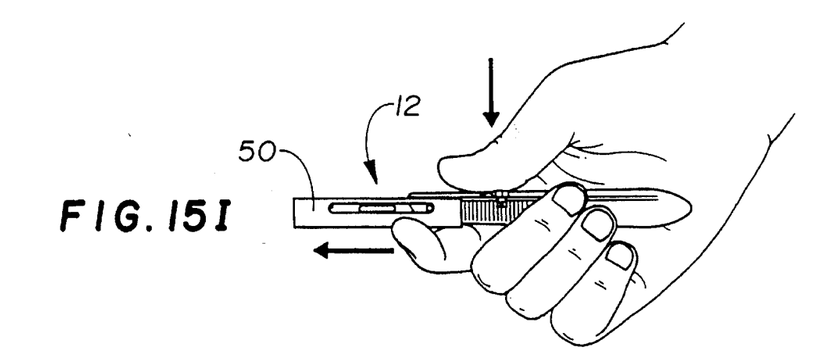
Figure 15J:
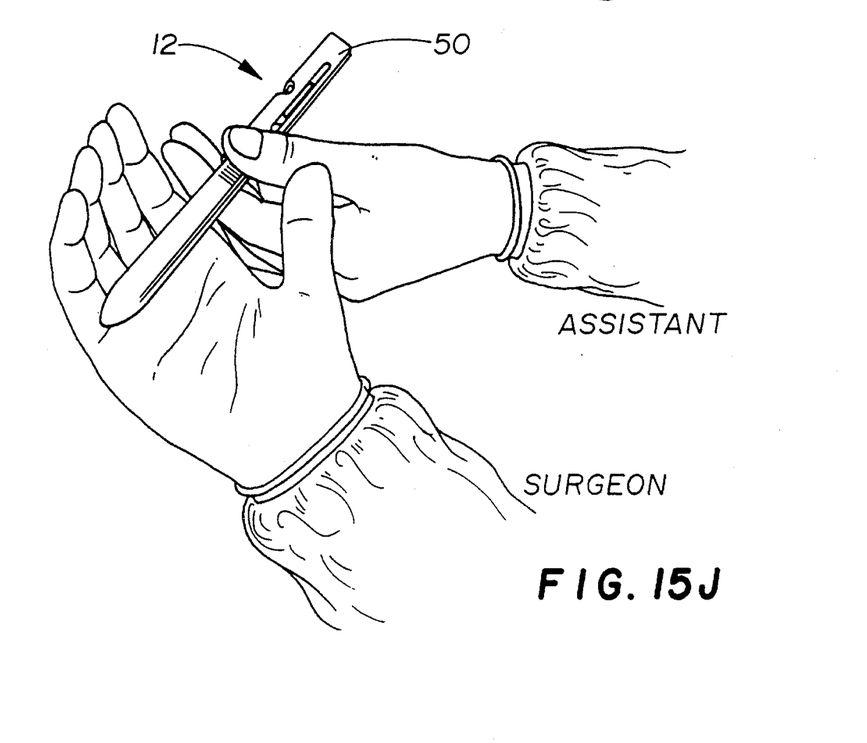
Figure 16:
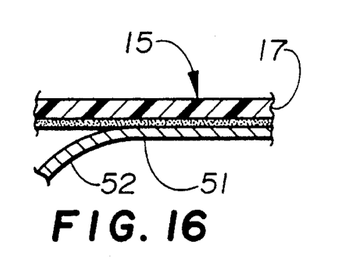
FIG. 16 is a section view, taken across the lines 16—16 of FIG. 15C, and showing an adhesive layer on the bottom of the blade dispenser to enable the blade dispenser to be removably mounted on a tray in the operating room.
Figure 17:
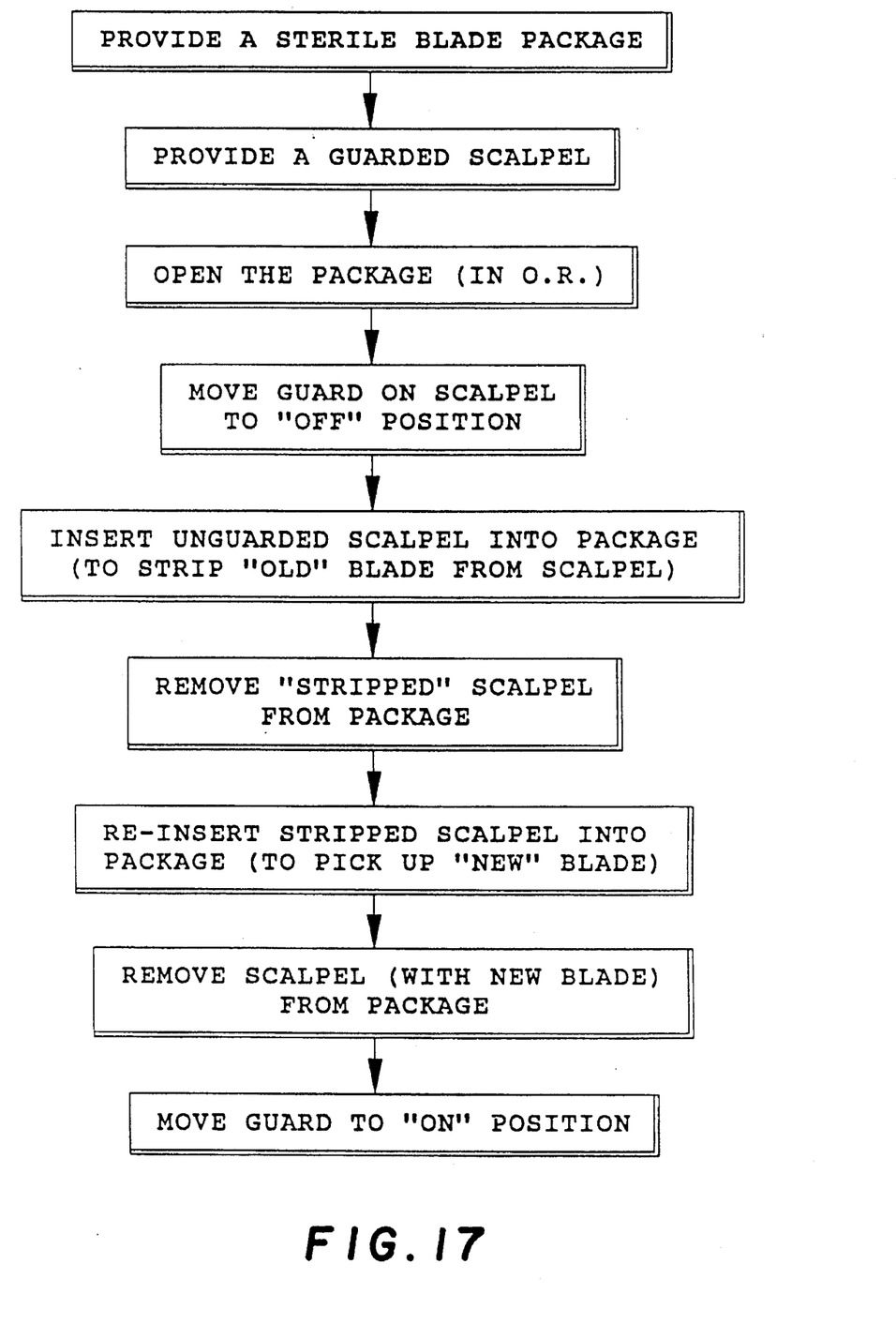
FIG. 17 is a flow chart illustrating the steps of the improved method of the present invention, as shown in the schematic sequence of FIGS. 15A–15J.

With reference to FIGS. 15A–15J and with further reference to FIGS. 16 and 17, the inherent features and advantages of the present invention will be more readily appreciated.

As shown in FIG. 15A, the present invention finds more particular utility with the guarded scalpel $12^1$ having a guard 50. In FIGS. 15B and 15C, the sterile blade package 13 is removed to uncover the blade dispenser 14. The bottom wall 17 of the blade dispenser 14 may contain an adhesive 51 protected by a cover 52 (as shown in FIG. 16) and the cover 52 may be pulled away to enable the blade dispenser 14 to be removably mounted on the tray or cart 11 by means of the adhesive 51. In FIG. 15D, the guard 50 on the guarded scalpel $12^1$ is manually retracted (in a one-hand operation) to expose the used or dulled blade 35.

Thereafter, as shown in FIG. 15E, the scalpel $12^1$ is inserted into the blade dispenser 14 and withdrawn therefrom (FIG. 15F) to remove the "old" or used blade 35 from the scalpel $12^1$. The scalpel $12^1$ is then re-inserted into the blade dispenser 14 (as shown in FIG. 15G) and withdrawn therefrom (FIG. 15H) to pick up a "new" or unused blade 35.

The guard 50 is moved forwardly to cover the blade 35 (FIG. 15I) and the guarded scalpel $12^1$ is transferred from the assistant to the surgeon (FIG. 15J). This sequence is illustrated in the flow chart of FIG. 17.

As a result, the hazards of being cut or nicked while removing an old blade and mounting a new blade on the scalpel, or while transferring the scalpel during a surgical procedure, are substantially reduced (if not eliminated altogether). The risk —that health care providers will inadvertently acquire a virus or other blood-borne infectious disease during a surgical procedure—is considerably reduced. Additionally, this avoids periodic AIDS testing and counseling, which is both costly and inconvenient. Moreover, the anxiety levels of health care providers will be substantially reduced. Indeed, these present anxiety levels result in a kind of "Russian roulette" mentality, so that becoming infected becomes an accepted occupational hazard. That is distracting to the health care providers. The present invention alleviates those anxieties and distractions.

Obviously, many modifications may be made without departing from the basic spirit of the present invention.

For example, the sterile blade dispenser may be packaged as part of an overall kit. Moreover, the teachings of the present invention are not confined to the specific surgical blade disclosed herein, but are applicable to a wide variety of surgical blades; thus a plurality of blade dispensers may be used during a surgical procedure.

Also, in lieu of the adhesive to hold down the blade dispenser 14, it would be possible to hold the blade dispenser in one hand and to hold the scalpel in the other hand, while inserting the scalpel into the housing of the blade dispenser or else moving the housing over the scalpel.

Accordingly, it will be appreciated by those skilled in the art that within the scope of the appended claims, the invention may be practiced other than has been specifically described herein.

We claim:

1. In a surgical procedure in an operating room, the method of changing blades on a scalpel during the surgical procedure and transferring the scalpel from an assistant to a surgeon and vice-versa during the procedure to avoid inadvertent cuts and assuring that the blade on the scalpel will be exposed only during actual use by the surgeon during the surgical procedure, comprising the steps of providing a sterile blade package, the sterile blade package having a housing provided with a plurality of sterile blades therein, providing a guarded scalpel having a movable guard, opening the sterile blade package in the operating room, moving the guard on the scalpel to an unguarded "off" position, inserting the unguarded scalpel into the housing to mount a sterile blade thereon, using the scalpel in its unguarded position during the operating procedure, moving the guard on the scalpel to its guarded "on" position when transferring the scalpel in the operating room, continue using the scalpel until the blade becomes dull or used, moving the guard into its unguarded "off" position and re-inserting the scalpel into the housing to strip the used blade from the scalpel, removing the stripped scalpel from the housing, re-inserting the stripped scalpel into the housing to pick up another sterile blade, removing the scalpel with the new sterile blade from the housing, moving the guard on the scalpel to a guarded "on" position, and repeating the process as needed; and further providing a means to prevent dulling of the sterile blade in the housing, comprising a deflectable wall within the housing, the deflectable wall having a hook formed thereon, and the sterile blade having a hole receiving the hook, such that the sterile blade is positioned within the housing; and such that when the stripped scalpel is reinserted into the housing, the stripped scalpel deflects the deflectable wall and separates the hook on the wall from the hole in the sterile blade, thereby releasing the sterile blade and enabling the sterile blade to be mounted on the scalpel and removed from the housing.

2. In a surgical procedure on a patient in an operating room staffed by a plurality of health care providers, the method of avoiding inadvertent or accidental cuts or nicks when using a scalpel and when changing the blade on the scalpel, comprising the steps of providing a scalpel having a blade mounted thereon and further having a moveable guard for covering the blade, alternately moving the guard to expose the blade and to cover the blade, respectively, such that the blade is exposed only when being used on the patient, and such that the blade is covered when the scalpel is being transferred from one health care provider to another in the operating room, continuing until the blade becomes dull and must be replaced, stripping the blade from the scalpel, providing a blade package having at least one sterile blade, the blade package including a deflectable wall and further including a member received in a hole in the sterile blade, thereby positioning the sterile blade in the blade package and preventing inadvertent dulling of the sterile blade in the blade package, opening the blade package and inserting the scalpel into the blade package to deflect the deflectable wall away from the sterile blade and to enable the sterile blade to be mounted on the scalpel as the hole in the blade clears the member in the blade package, such that the scalpel with the sterile blade mounted thereon may be removed from the package, and such that the deflectable wall in the blade package may return substantially to its original position.

3. The method of claim 2, wherein the scalpel has a cleat provided with at least one groove, and wherein the blade has a slotted opening received in the groove formed in the cleat on the scalpel.

4. The method of claim 3, wherein the cleat has a pair of opposing grooves, and wherein the slotted opening in the blade has a narrowed forward portion received in the grooves.

* * * * *